United States Patent
Dai et al.

(10) Patent No.: US 11,540,788 B2
(45) Date of Patent: Jan. 3, 2023

(54) MEDICAL IMAGING SYSTEM, METHOD FOR IDENTIFYING BODY POSITION OF DETECTION OBJECT, AND STORAGE MEDIUM

(71) Applicant: GE Precision Healthcare LLC, Wauwatosa, WI (US)

(72) Inventors: Qingyu Dai, Beijing (CN); Qilin Lu, Beijing (CN); Yaan Ge, Beijing (CN); Kun Wang, Beijing (CN); Longqing Wang, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 221 days.

(21) Appl. No.: 17/074,849

(22) Filed: Oct. 20, 2020

(65) Prior Publication Data
US 2021/0128084 A1 May 6, 2021

(30) Foreign Application Priority Data
Oct. 31, 2019 (CN) .......................... 201911050865.8

(51) Int. Cl.
| | | |
|---|---|---|
| G06K 9/00 | (2022.01) | |
| A61B 6/04 | (2006.01) | |
| G06N 3/02 | (2006.01) | |
| A61B 6/00 | (2006.01) | |
| G06T 7/70 | (2017.01) | |
| G06T 7/00 | (2017.01) | |

(52) U.S. Cl.
CPC ................ *A61B 6/04* (2013.01); *A61B 6/488* (2013.01); *A61B 6/5223* (2013.01); *G06N 3/02* (2013.01); *G06T 7/0012* (2013.01); *G06T 7/70* (2017.01); *G06T 2207/20081* (2013.01); *G06V 2201/034* (2022.01)

(58) Field of Classification Search
CPC .................................................... G06N 3/0454
See application file for complete search history.

(56) References Cited

U.S. PATENT DOCUMENTS

| | | | | |
|---|---|---|---|---|
| 2018/0137244 | A1* | 5/2018 | Sorenson | G16H 30/20 |
| 2018/0259608 | A1* | 9/2018 | Golden | G06N 3/02 |
| 2018/0315188 | A1* | 11/2018 | Tegzes | G06T 7/0012 |
| 2019/0073569 | A1* | 3/2019 | Ben-Ari | A61B 5/7267 |

OTHER PUBLICATIONS

Authors et al, "Deep Learning Based Simplification of Scan Input Workflow," IP.com No. IPCOM000250798D, Sep. 5, 2017, 4 pages.
Bertrand et al., "Classification of MRI data using Deep Learning and Gaussian Process-based Model Selection," arXiv preprint arXiv:1701.04355, Jan. 16, 2017, 4 pages.

(Continued)

*Primary Examiner* — Hadi Akhavannik (57) ABSTRACT

Embodiments of the present invention provide a method for identifying a body position of a detection object in medical imaging, a medical imaging system, and a computer-readable storage medium. The method comprises: receiving an image group by a trained deep learning network, the image group comprising a plurality of pre-scan images in a plurality of directions obtained by pre-scanning a detection object; and outputting body position information of the detection object by the deep learning network.

11 Claims, 3 Drawing Sheets

(56) References Cited

OTHER PUBLICATIONS

Kabani et al., "Object Detection and Localization Using Deep Convolutional Networks with Softmax Activation and Multi-class Log Loss." 9730. 358-366. 10.1007/978-3-319-41501-7_41, (2016), 9 pages.
Roth et al., "Anatomy-specific classification of medical images using deep convolutional nets," in IEEE 12th International Symposium on Biomedical Imaging (ISBI), pp. 101-104, Brooklyn Bridge, NY, USA, Apr. 2015, 4 pages.

* cited by examiner

MEDICAL IMAGING SYSTEM, METHOD FOR IDENTIFYING BODY POSITION OF DETECTION OBJECT, AND STORAGE MEDIUM

CROSS-REFERENCE TO RELATED APPLICATIONS

This application claims the benefit of Chinese Patent Application No. 201911050865.8 filed on Oct. 31, 2019, the disclosure of which is herein incorporated by reference in its entirety.

TECHNICAL FIELD

The present invention relates to medical imaging techniques, and more specifically, to a method for identifying a body position of a detection object in medical imaging and a computer-readable storage medium.

BACKGROUND

In medical imaging techniques such as magnetic resonance imaging (MRI) and computed tomography (CT) imaging, it is usually needed to set body position information of a patient during scanning so as to determine the anatomical section direction (for example, a coronal direction, a sagittal direction, and a transverse direction) of an image. Such body position information includes, for example, the orientation of the head or feet (for example, expressed as whether the head or the feet enters the scanning area first when the patient is moved to the scanning area) and a lying posture (for example, a supine position, a prone position, a left decubitus position, and a right decubitus position) of the patient. However, an operator (such as a doctor or a technician) performing the imaging-scanning often wants to reduce the need for manual configuration as much as possible to reduce complexity and time consumption, thereby preventing more serious problems caused by information input errors. For example, when an obtained image contains wrong information, it cannot be used in diagnosis and needs to be manually modified or even re-scanned.

SUMMARY

An embodiment of the present invention provides a method for identifying a body position of a detection object in medical imaging. The method comprises: receiving an image group by a trained deep learning network, the image group comprising a plurality of pre-scan images in a plurality of directions obtained by pre-scanning a detection object; and outputting body position information of the detection object by the deep learning network.

An embodiment of the present invention further provides a computer-readable storage medium, for storing a computer program, wherein when executed by a computer, the computer program causes the computer to perform the method described above.

An embodiment of the present invention further provides a medical imaging system, comprising a controller unit, wherein the controller unit is configured to control a trained deep learning network to receive an image group, and receive body position information of a detection object that is output by the deep learning network, the image group comprising a plurality of pre-scan images in a plurality of directions obtained by pre-scanning the detection object by the medical imaging system.

Other features and aspects will become clear through the following detailed description, accompanying drawings and claims.

BRIEF DESCRIPTION OF THE DRAWINGS

The present invention may be better understood by describing exemplary embodiments of the present invention with reference to accompanying drawings, in which.

DETAILED DESCRIPTION OF THE EMBODIMENTS

Specific implementation manners of the present invention will be described in the following. It should be noted that during the specific description of the implementation manners, it is impossible to describe all features of the actual implementation manners in detail in this description for the sake of brief description. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second" and similar words used in the description and claims of the patent application of the present invention do not denote any order, quantity or importance, but are merely intended to distinguish between different constituents. "One," "a(n)" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

Some embodiments of the present invention can automatically identify body position information of an imaged detection object based on a deep learning technology, so that the identified body position information can be further used to determine direction information of scan images in the imaging process. Thus, the operator does not need to manually set the body position information in the imaging process of the detection object. The operation workload is reduced, and input of wrong body position information by mistake is avoided. These embodiments can be applied to magnetic resonance imaging techniques. For example, instead of providing a body position selection/input window on an operation interface of a magnetic resonance imaging system, body position information is automatically identified using images obtained when a detection object is pre-scanned. These embodiments can further be applied to other imaging techniques such as CT, PET, and SPECT in a similar and reasonable manner.

As discussed herein, the deep learning technology (also referred to as deep machine learning, hierarchical learning, deep structured learning, or the like) can employ a deep learning network (for example, an artificial neural network) to process input data and identify information of interest. The deep learning network may be implemented using one or a plurality of processing layers (such as an input layer, a normalization layer, a convolutional layer, a pooling layer, and an output layer, where processing layers of different numbers and functions may exist according to different deep learning network models), where the configuration and number of the layers allow the deep learning network to process complex information extraction and modeling tasks. Specific parameters (or referred to as "weight" or "bias") of the network are usually estimated through a so-called learning process (or training process). The learned or trained parameters usually result in (or output) a network corresponding to layers of different levels, so that extraction or simulation of different aspects of initial data or the output of a previous layer usually may represent the hierarchical structure or concatenation of layers. During image processing or reconstruction, this may be represented as different layers with respect to different feature levels in the data. Thus, processing may be performed layer by layer. That is, "simple" features may be extracted from input data for an earlier or higher-level layer, and then these simple features are combined into a layer exhibiting features of higher complexity. In practice, each layer (or more specifically, each "neuron" in each layer) may process input data as output data for representation using one or a plurality of linear and/or non-linear transformations (so-called activation functions). The number of the plurality of "neurons" may be constant among the plurality of layers or may vary from layer to layer.

As discussed herein, as part of the initial training in a deep learning process to solve a specific problem, a training data set includes a known input value (for example, a medical image with RGB depth information or a pixel matrix of the medical image subjected to coordinate transformation) and an expected (target) output value (for example, body position information of the detection object in the image or image class information including the body position information) that is finally output in the deep learning process. In this manner, a deep learning algorithm can process the training data set (in a supervised or guided manner or an unsupervised or unguided manner) until a mathematical relationship between a known input and an expected output is identified and/or a mathematical relationship between the input and output of each layer is identified and represented.

In the learning process, (part of) input data is usually used, and a network output is created for the input data. Afterwards, the created network output is compared with the expected output of the data set, and then a difference between the created and expected outputs is used to iteratively update network parameters (weight and/or bias). A stochastic gradient descent (SGD) method may usually be used to update network parameters. However, those skilled in the art should understand that other methods known in the art may also be used to update network parameters. Similarly, a separate validation data set may be used to validate a trained learning network, where both a known input and an expected output are known. The known input is provided to the trained learning network so that a network output can be obtained, and then the network output is compared with the (known) expected output to validate prior training and/or prevent excessive training.

Figure 1:
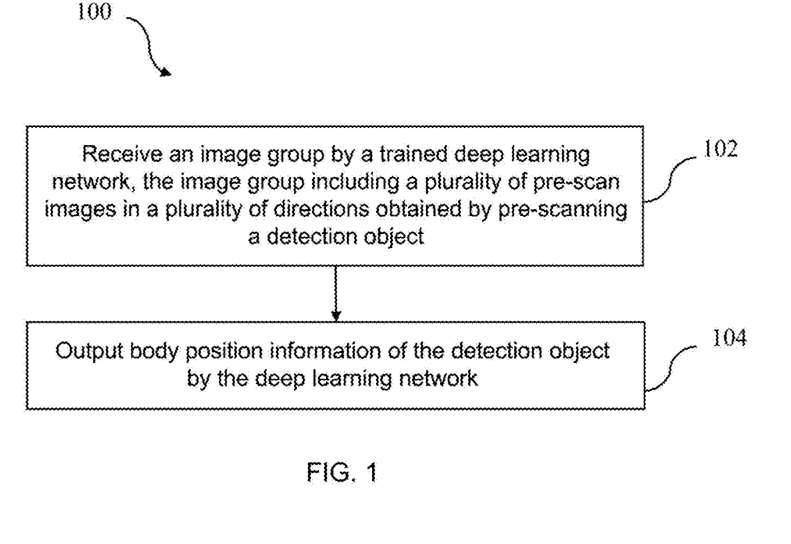
FIG. 1 is a flowchart of a method for identifying a body position of a detection object in medical imaging according to an embodiment of the present invention.

FIG. 1 is a flowchart of a method 100 for identifying a body position of a detection object in medical imaging according to some embodiments of the present invention. As shown in FIG. 1, the method 100 includes steps S102 and S104.

Step S102: receive an image group by a trained deep learning network, the image group including a plurality of pre-scan images in a plurality of directions obtained by pre-scanning a detection object.

Using magnetic resonance imaging as an example, generally, a series of images may be reconstructed by performing pre-scanning (or positioning scanning or basic scanning) on a detection object. This series of images include, for example, 15 (or other numbers) pre-scan images, and each pre-scan image has direction information that can be identified (for example, based on preset body position information of the detection object). Those skilled in the art should understand that the direction information is used to describe the direction of the anatomical plane of the human body, which may include three basic directions such as a coronal direction, a sagittal direction, and a transverse direction.

The plurality of directions in step S102 includes the coronal direction, the sagittal direction, and the transverse direction. That is, the image group received by the deep learning network includes images in three directions such as coronal pre-scan images, sagittal pre-scan images, and transverse pre-scan images. For example, the aforementioned 15 pre-scan images may include 5 coronal image, 5 sagittal images, and 5 transverse images.

The trained deep learning network has the ability to identify the body position of the detection object according to the group of pre-scan images. Moreover, in step S104, body position information of the detection object is output by the deep learning network.

Step S104 may specifically include: determining one body position type selected from a plurality of predetermined body position types to serve as the body position information of the detection object. For example, the deep learning network may process the plurality of received pre-scan images to determine the body position type that the body position of the detection object most probably belongs to.

The deep learning network may be implemented through preparation of training data, selection and construction of a network model, and training, testing, and optimization of the network.

The training data may be medical scan images, such as magnetic resonance pre-scan images. Specifically, the training data may include, for example, images obtained when magnetic resonance pre-scanning is performed at a plurality of known (or determined) body positions for a plurality of regions of interest (for example, the abdomen, chest, heart, and head) of the human body. In an embodiment, the aforementioned deep learning network is obtained by data training using these images as input of the network model, and using the plurality of corresponding known body positions as output of the network model.

For example, when performing data training, a plurality of commonly used body position types may be used as output of the deep learning network, where each body position type includes a combination of an orientation of a head or feet of the detection object and one position selected from the group consisting of a supine position, a prone position, a left decubitus position, and a right decubitus position. For example, these body position types may include, for example, eight body positions shown in FIG. 2, where HFS represents Head First, Supine; HFP represents Head First, Prone; HFDR represents Head First, Right Decubitus; HFDL represents Head First, Left Decubitus; FFS represents Feet First, Supine; FFP represents Feet first, Prone; FFDR represents Feet First, Right Decubitus; FFDL represents Feet First, Left Decubitus. "Feet First" represents that the feet of the detection object are close to the scanning area (for example, the scanning chamber) when the detection object is on the detection table, and the feet of the detection object enter the scanning area first when the detection table is moved to make the detection object thereon enter the scanning chamber from the outside. The same logic can be applied to the definition of "Head First."

Figure 2:
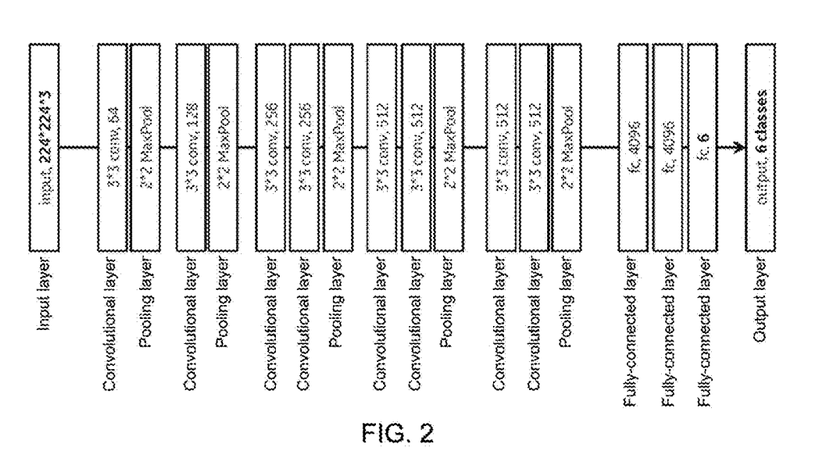
FIG. 2 is an architectural diagram of an example of a VGG convolutional neural network.

In some embodiments, the deep learning network is trained based on a VGGNet (Visual Geometry Group Network) convolutional neural network or other well-known models. For example, a VGG-11 network may be selected to implement the embodiment of the present invention. FIG. 2 is a schematic architectural diagram of the VGG-11 network, which specifically includes an input layer, an output layer, 5 groups of convolutional layers (a total of 8 convolutional layers) located between the input layer and the output layer, and 3 fully-connected layers, where each group of convolutional layers is further connected to a pooling layer. The size of each convolution kernel is 3×3 (pixels), the size of each pooling kernel is 2×2 (pixels), and the number of convolution kernels in each group of convolutional layers is separately 64, 128, 256, 512, and 512. In training, a large number of image groups are input to the deep learning network. Each image group includes a plurality of images having the same known body position type (for example, each image group is an image group obtained by one pre-scan or scan), the size of each image may be, for example, 224×224×3. The known body position type is accordingly set as output of the deep learning network (or as will be described later—a large number of images having a known image class are input to the deep learning network, and the known image class is accordingly used as output of the deep learning network). The weight at each pixel in each layer and other required parameters are determined by convolutional learning to identify a mathematical relationship between the known input and output and/or represent a mathematical relationship between the input and output of each layer, so as to establish a deep learning network capable of identifying a body position (or an image class). Each convolutional layer is used to perform convolution processing on image data output by an upper level, so as to obtain a feature map of the convolutional layer. The pooling layer is used to perform, for example, max-pooling on the feature map of the upper-layer convolutional layer to extract main features. The fully-connected layer is used to integrate the upper-layer feature map, and the output layer is used to output a judgment result (i.e., body position information or the image class described below) obtained by, for example, logistic regression processing.

In the learning process, comparison may be performed based on the network output (body position information or image class) corresponding to the known input (pre-scan image group) and actual information (known body position information or image class), and a difference thereof is a loss function. The loss function may be used to iteratively update parameters (weight and/or to bias) of the network so that the loss function continuously decreases to train a neural network model with higher accuracy. In some embodiments, many functions can be used as the loss function, including, but not limited to, mean squared error (mean squared), cross entropy error, and the like.

Figure 3:
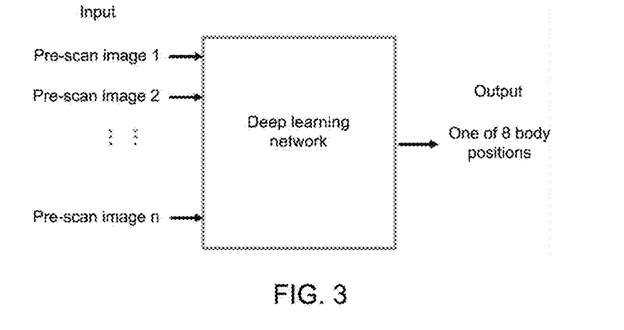
FIG. 3 is a schematic diagram of using a separate deep learning network to output body position information.

FIG. 3 is a schematic diagram of using a separate deep learning network to output body position information. As shown in FIG. 3, in an embodiment, during a process such as magnetic resonance scanning, a series of obtained pre-scan images may be input to an input layer of the deep learning network, and then these images are processed based on parameters such as the weight determined in the training process, so as to output, on the output layer, a body position type of a detection object currently being scanned.

Figure 4:
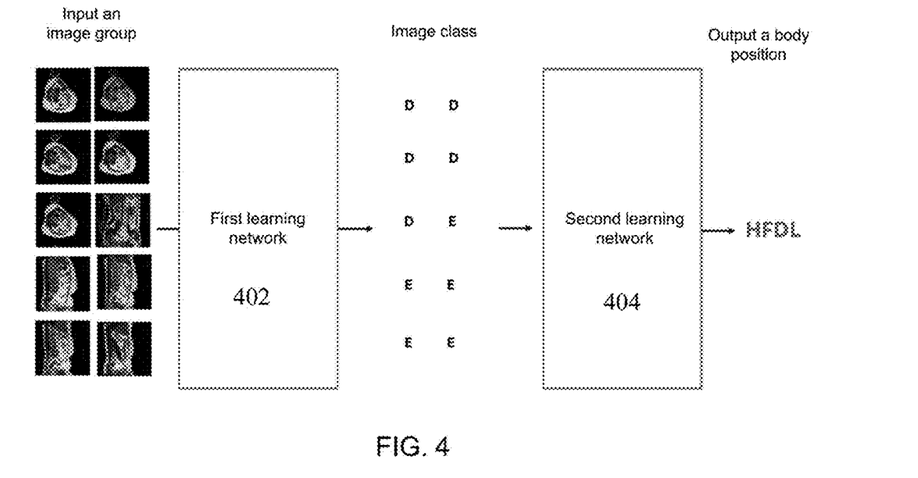
FIG. 4 is a schematic diagram of using a first learning network and a second learning network that are cascaded to output body position information.

FIG. 4 is a schematic diagram of using a first learning network and a second learning network that are cascaded to output body position information. As shown in FIG. 4, the aforementioned deep learning network may include a first learning network 402 and a second learning network 404, the first learning network 402 may have the aforementioned VGG-11 architecture or a similar architecture, and the second learning network 404 may be a classifier having a simple architecture.

The first learning network 402 is configured to receive the aforementioned image group and output an image class of each pre-scan image. The image class includes a combination of at least one direction selected from the aforementioned plurality of directions (the coronal direction, sagittal direction, and transverse direction) and at least one body position type selected from the plurality of body position types (HFS, HFP, HFDR, HFDL, FFS, FFP, FFDR, and FFDL). That is, the first learning network 402 can be used to judge possible directions of the pre-scan images and possible body positions of the detection object therein.

In training, the input layer of the first learning network 402 receives a plurality of images with a size of, for example, 256×256×3, and a known image class corresponding to each image is set on the output layer, and the weight at each pixel in each layer and other required parameters are determined by convolutional learning, so as to establish a deep learning network capable of identifying an image class.

Thus, in magnetic resonance scanning, a series of obtained pre-scan images may be input to the input layer of the first deep learning network, and then these images are processed based on the parameters such as the weight determined in the training process, so as to output, on the output layer, an image class of each pre-scan image.

The aforementioned image class may be one image class selected from a plurality of known image classes in the following table:

Class A: A combination of the transverse direction, HFS, and FFS, which indicates that the pre-scan image is a transverse image, where the body position of the detection object is HFS or FFS;

Class B: A combination of the transverse direction, HFP, and FFP, which indicates that the pre-scan image is a transverse image, where the body position of the detection object is HFP or FFP;

Class C: A combination of the transverse direction, HFDR, and FFDL, which indicates that the pre-scan image is a transverse image, where the body position of the detection object is HFDR or FFDL;

Class D: A combination of the transverse direction, HFDL, and FFDR, which indicates that the pre-scan image is a transverse image, where the body position of the detection object is HFDL or FFDR;

Class E: A combination of the sagittal direction, the coronal direction, HFS, HFP, HFDR, and HFDL, which indicates that the pre-scan image is a sagittal image or coronal image, where the body position of the detection object is HFS, HFP, HFDR, or HFDL;

Class F: A combination of the sagittal direction, the coronal direction, FFS, FFP, FFDR, and FFDL, which indicates that the pre-scan image is a sagittal image or coronal image, where the body position of the detection object is FFS, FFP, FFDR, or FFDL.

The foregoing classification manner of image classes helps to obtain accurate body position information. Certainly, the embodiment of the present invention may further employ image classes of other numbers and classification manners to train the aforementioned first learning network and second learning network, so as to obtain more accurate body position information or achieve other beneficial effects.

In training, the second learning network 404 may receive known image types of image groups generated in a plurality of pre-scanning processes, and set, on the output layer, a body position of the detection object for performing each pre-scan. The weight at each pixel in each layer and other required parameters are determined by convolutional learning, so as to establish a second learning network capable of identifying a body position based on an image class.

Thus, after the first learning network 402 outputs the image class of each pre-scan image to the second learning network, the second learning network 404 may output the body position information of the detection object.

First, the first learning network 402 analyzes an input image group to obtain an image class of each pre-scan image, where at least the possible direction and body position type of each pre-scan image can be obtained according to the image class, and then the second learning network 404 analyzes the image class of each input pre-scan image, so that correct body position information of the detection object can be obtained. In this way, the accuracy of body position identification can be greatly improved. For example, at least the problem of accuracy reduction due to the excessively large computation amount can be avoided.

For example, if the first learning network 402 receives 10 pre-scan images and outputs image classes of the first to the tenth pre-scan images including 4 image classes being Class D and 6 image classes being Class E, the second learning network 404 can output the accurate body position of the detection object, namely, HFDL.

Further, the second learning network 404 is configured to extract an image class of a smaller number from received image classes, and correct the extracted image class to be consistent with an image class of a larger number in the received image classes. This may be accomplished by setting a preprocessing layer in the second learning network 404. First, an image class of each pre-scan image is output, so that there is a chance to correct wrong image classes in the second learning network 404, so that the finally output body position information has high accuracy.

For example, if the first learning network 402 receives 10 pre-scan images and outputs image classes of the first to the tenth pre-scan images including 3 image classes being Class D, 6 image classes being Class E, and 1 image class being Class C, the second learning network 404 corrects Class C to Class D or Class E through preprocessing, and then processes preprocessed data to output the accurate body position of the detection object, namely, HFDL.

Further, the second learning network 404 judges the direction in the image class of the smaller number and corrects the image class to an image class of a larger number including the direction. That is, the modified image class of the smaller number and the image class of the larger number have the same direction. For example, since the direction in Class C is the transverse direction, Class C is corrected to Class D which is pointing to the transverse direction rather than Class E which is pointing to the sagittal direction.

In the medical imaging-scanning process, when the pre-scanning ends, formal scanning may be performed on a detection object to obtain a plurality of medical diagnostic images of the detection object. Thus, after body position information of the detection object is identified based on any embodiment of the method 300 and medical diagnostic images are obtained based on formal scanning, direction information of each medical diagnostic image may be determined based on the identified body position information.

The body position of the detection object is automatically identified, so that even if a doctor or a technician is no longer required to manually set body position information, direction information of each reconstructed image can be determined as in the conventional scanning process. The scanning process is smoother, and the scanning result also has higher robustness. For example, a medical imaging system may judge the direction of a corresponding pre-scan image based on automatically identified body position information, HFS (Head First, Supine), and an employed scanning sequence.

Figure 5:
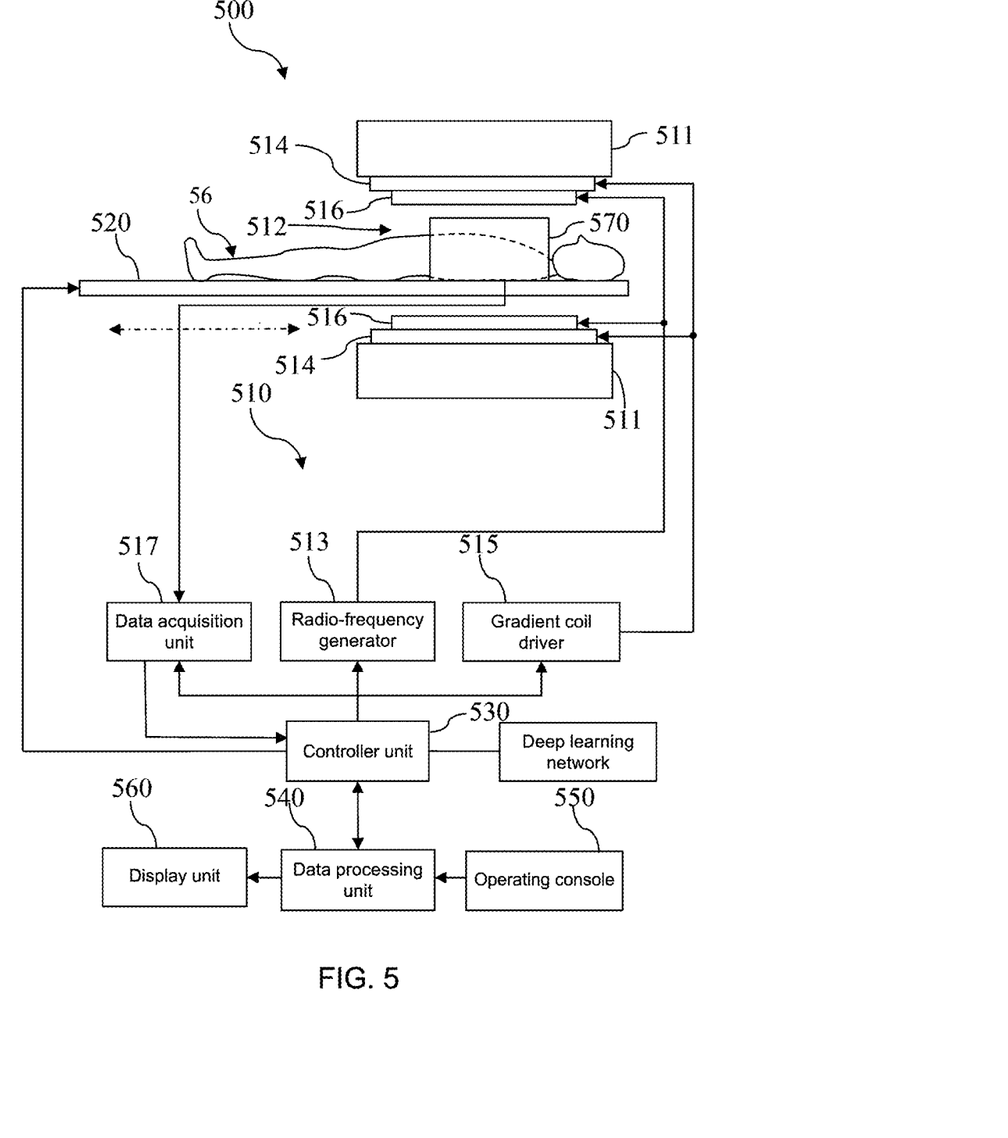
FIG. 5 is a structural diagram of an example of a magnetic resonance imaging-scanning system.

The method described above can be used in magnetic resonance or other medical imaging-scanning techniques. FIG. 5 is a structural diagram of an example of a magnetic resonance imaging-scanning system. An example of applying the aforementioned medical imaging-scanning method to a magnetic resonance imaging-scanning technique will be described below with reference to FIG. 5.

As shown in FIG. 5, the magnetic resonance imaging system 500 includes a scanner 510, a table 520, a controller unit 530, a data processing unit 540, an operating console 550, and a display unit 560.

In an example, the scanner 510 may include a main magnet assembly 511. The main magnet assembly 511 usually includes an annular superconducting magnet defined in a housing, where the annular superconducting magnet is mounted in an annular vacuum container. The annular superconducting magnet and the housing thereof define a cylindrical space, i.e., the scanning chamber 512 shown in FIG. 5, which surrounds the detection object 56. The scanning chamber 512 defines an imaging area of the magnetic resonance imaging system or at least part of the imaging area.

The table 520 is configured to be communicable with a patient entrance of the scanning chamber 512 and is configured to carry the detection object 56, so that the detection object 56 in a specific body position (for example, one body position type selected from the aforementioned plurality of body position types) can be moved to the scanning area to receive imaging-scanning.

The scanner 510 further includes an RF transmit coil 516, a radio-frequency generator 513, a gradient coil assembly 514, a gradient coil driver 515, an RF receive coil 570, and a data acquisition unit 517. When an imaging-scanning process is performed on the detection object 56, the scanner 510 is configured to obtain image data of the detection object 56.

The image data may be processed, such as calculated or reconstructed, by the data processing unit 540. The data processing unit 540 may include a computer and a storage medium, where a program of predetermined data processing to be executed by the computer is recorded on the storage medium.

The controller unit 530 is coupled to the scanner 510, the table 520, and the data processing unit 540 to control these components to perform a scanning process for magnetic resonance imaging. The scanning process may specifically include a pre-scanning process and a formal scanning process.

The controller unit 530 may include a computer and a storage medium, where the storage medium is configured to store a program executable by the computer, and when the computer executes the program, the components such as the scanner 510, the table 520, and the display unit 560 are enabled to perform corresponding operations in the pre-scanning process and the scanning process. The data processing unit 540 is also enabled to perform predetermined data processing.

The storage media of the controller unit 530 and the data processing unit 540 may include, for example, a ROM, a floppy disk, a hard disk, an optical disk, a magneto-optical disk, a CD-ROM, or a non-volatile memory card.

The operating console 550 may include a user input device, such as a keyboard and a mouse, where an operator may input control signals or parameter settings to the controller unit 530 through the user input device, and these parameter settings usually include setting of body position information of the detection object. However, this step may be omitted in this embodiment; instead, the body position information of the detection object is automatically identified by the deep learning network.

The display unit 560 may be connected to the operating console 550 to display an operation interface that includes a parameter setting interface, and may further be connected to the data processing unit 540 to display reconstructed images or various images captured by a camera that is coupled to the magnetic resonance imaging system.

In performing magnetic resonance imaging-scanning, a doctor or a technician usually needs to assist or instruct the detection object to be positioned on the table 520 according to a desired body position. Then, body position information of the detection object is set on the operation interface before pre-scanning is performed, and if the set body position information is inconsistent with the actual positioning posture of the detection object, it takes time to fix such errors, or requires a re-scanning.

By using the method of the present invention, the body position is not set; instead, the body position is determined as follows: first, pre-scanning is performed by the scanner to obtain a group of pre-scan images; then, the pre-scan images are used to identify a body position of a detection object; after a region of interest is determined based on the pre-scan images, formal scanning may be performed on the region of interest; the data processing unit 540 reconstructs a medical diagnostic image based on data obtained in formal scanning; and direction information of the medical diagnostic image may be marked while the medical diagnostic image is displayed by the display unit. As a result, the doctor would not be confused with the direction of the image even if the body position is not set.

In an embodiment, the aforementioned trained deep learning network is obtained based on training by a training system on an external carrier (for example, a device other than the medical imaging system). In some embodiments, the training system may include a first module configured to store a training data set, a second module configured to perform training and/or update based on a model, and a network configured to connect the first module and the second module. In some embodiments, the first module includes a first processing unit and a first storage unit, where the first storage unit is configured to store the training data set, and the first processing unit is configured to receive a relevant instruction (for example, obtaining a training data set) and send the training data set to the second module according to the instruction. The second module includes a second processing unit and a second storage unit, where the second storage unit is configured to store a training model, and the second processing unit is configured to receive a relevant instruction and perform training and/or update of the learning network. In some embodiments, the network may include various connection types, such as wired or wireless communication links, or fiber-optic cables.

Once a deep learning network is generated and/or configured, the data thereof can be replicated and/or loaded into the aforementioned magnetic resonance imaging system 500, which may be accomplished in a different manner. For example, models may be loaded via a directional connection or link between the controller unit 530 of the magnetic resonance imaging system 500 and the second storage unit. In this regard, communication between different elements may be accomplished using an available wired and/or wireless connection and/or based on any suitable communication (and/or network) standard or protocol. Optionally, the data may be indirectly loaded into the magnetic resonance imaging system 500. For example, the data may be stored in a suitable machine-readable medium (for example, a flash memory card), and then the medium is used to load the data into the magnetic resonance imaging system 500 (for example, by a user or an authorized person of the system on site). Alternatively, the data may be downloaded to an electronic device (for example, a notebook computer) capable of local communication, and then the device is used on site (for example, by a user or an authorized person of the system) to upload the data to the magnetic resonance imaging system 500 via a direct connection (for example, a USB connector).

Based on the above description, an embodiment of the present invention may further provide a medical imaging system, including a controller unit, where the controller unit is configured to control a trained deep learning network to receive an image group, and receive body position information of a detection object that is output by the deep learning network, the image group including a plurality of pre-scan images in a plurality of directions obtained by pre-scanning the detection object by the medical imaging system.

The deep learning network is specifically configured to determine one body position selected from a plurality of predetermined body position types to serve as the body position information of the detection object.

The deep learning network may include a first learning network 402 and a second learning network 404. The first learning network 402 is configured to receive the image group, and output an image class of each pre-scan image, the image class including a combination of at least one direction selected from the plurality of directions and at least one body position type selected from the plurality of body position types. The second learning network 404 is configured to receive the image class of each pre-scan image, and output the body position information of the detection object.

The second learning network 404 is further configured to extract an image class of a smaller number from received image classes, and correct the extracted image class to be consistent with an image class of a larger number in the received image classes. The image class of the smaller number and the image class of the larger number include the same direction.

An embodiment of the present invention may further provide a computer-readable storage medium for storing an instruction set and/or a computer program. When executed by a computer, the instruction set and/or computer program causes the computer to perform the method for identifying a body position of a detection object according to any embodiment described above. The computer executing the instruction set and/or computer program may be a computer of a medical imaging system, or may be other apparatuses/modules of the medical imaging system. In an embodiment, the instruction set and/or computer program may be programmed into a processor/controller, for example, the aforementioned controller unit 530, of the computer.

Specifically, when executed by the computer, the instruction set and/or computer program causes the computer to:

identify an image quality type of a medical image based on a trained learning network; and generate, based on the identified image quality type, a corresponding control signal for controlling the medical imaging system.

The instructions described above may be combined into one instruction for execution, and any of the instructions may also be split into a plurality of instructions for execution. Moreover, the present invention is not limited to the instruction execution order described above.

In some embodiments, before identifying an image quality type in a medical image, the method further includes receiving, based on an instruction of a user, the medical image generated by the medical imaging system.

As used herein, the term "computer" may include any processor-based or microprocessor-based system including a system that uses a microcontroller, a reduced instruction set computer (RISC), an application specific integrated circuit (ASIC), a logic circuit, and any other circuit or processor capable of executing the functions described herein. The above examples are merely exemplary and thus are not intended to limit the definition and/or meaning of the term "computer" in any way.

The instruction set may include various commands that instruct a computer acting as a processor or instruct a processor to perform particular operations, such as the methods and processes of various embodiments. The instruction set may be in the form of a software program, and the software program can form part of one or a plurality of tangible, non-transitory computer-readable media. The software may be in various forms such as system software or application software. In addition, the software may be in the form of a set of independent programs or modules, a program module within a larger program, or part of a program module. The software may also include modular programming in the form of object-oriented programming. The input data may be processed by the processor in response to an operator command, or in response to a previous processing result, or in response to a request made by another processor.

Some exemplary embodiments have been described above; however, it should be understood that various modifications may be made. For example, if the described techniques are performed in a different order and/or if the components of the described system, architecture, device, or circuit are combined in other manners and/or replaced or supplemented with additional components or equivalents thereof, a suitable result can be achieved. Accordingly, other implementation manners also fall within the protection scope of the claims.

The invention claimed is:

1. A method for identifying a body position of a detection object in medical imaging, comprising:
receiving an image group by a trained deep learning network, the image group comprising a plurality of pre-scan images in a plurality of directions obtained by pre-scanning a detection object;
outputting body position information of the detection object by the deep learning network;
wherein the outputting body position information of the detection object by the deep learning network comprises: determining one body position type from a plurality of predetermined body position types to serve as the body position information of the detection object;
wherein the deep learning network comprises a first learning network and a second learning network, the method comprising:
receiving the image group by the first learning network, and outputting an image class of each pre-scan image, the image class comprising a combination of at least one direction selected from the plurality of directions and at least one body position type selected from the body position types; and
receiving the image class of each pre-scan image by the second learning network, and outputting the body position information of the detection object.

2. The method according to claim 1, wherein the plurality of directions comprise a coronal direction, a sagittal direction, and a transverse direction, and each body position type comprises a combination of an orientation of a head or feet of the detection object and one position selected from the group consisting of a supine position, a prone position, a left decubitus position, and a right decubitus position.

3. The method according to claim 1, wherein the second learning network extracts an image class of a smaller number from received image classes, and corrects the extracted image class to be consistent with an image class of a larger number in the received image classes.

4. The method according to claim 3, wherein the image class of the smaller number and the image class of the larger number comprise the same direction.

5. The method according to claim 1, wherein the deep learning network comprises a VGG (Visual Geometry Group) convolutional neural network.

6. A computer-readable storage medium, for storing a computer program, wherein when executed by a computer, the computer program causes the computer to perform the method according to claim 1.

7. A medical imaging system, comprising a controller unit, wherein the controller unit is configured to control a trained deep learning network to receive an image group, and receive body position information of a detection object that is output by the deep learning network, the image group comprising a plurality of pre-scan images in a plurality of directions obtained by pre-scanning the detection object by the medical imaging system;

wherein the deep learning network is configured to determine one body position type selected from a plurality of predetermined body position types to serve as the body position information of the detection object; and wherein the deep learning network comprises a first learning network and a second learning network, the first learning network is configured to receive the image group and output an image class of each pre-scan image, the image class comprising a combination of at least one direction selected from the plurality of directions and at least one body position type selected from the body position types; and the second learning network is configured to receive the image class of each pre-scan image and output the body position information of the detection object.

8. The system according to claim 7, wherein the plurality of directions comprise a coronal direction, a sagittal direction, and a transverse direction, and each body position type comprises a combination of an orientation of a head or feet of the detection object and one position selected from the group consisting of a supine position, a prone position, a left decubitus position, and a right decubitus position.

9. The system according to claim 7, wherein the second learning network is configured to extract an image class of a smaller number from received image classes, and correct the extracted image class to be consistent with an image class of a larger number in the received image classes.

10. The system according to claim 9, wherein the image class of the smaller number and the image class of the larger number comprise the same direction.

11. The system according to claim 7, wherein the deep learning network comprises a VGG (Visual Geometry Group) convolutional neural network.

* * * * *